United States Patent [19]

Takago et al.

[11] Patent Number: 4,880,927
[45] Date of Patent: Nov. 14, 1989

[54] METHOD FOR PREPARING A CYCLIC ISOCYANURIC ESTER HAVING ORGANOSILICON GROUPS

[75] Inventors: Toshio Takago, Annaka; Yasushi Yamamoto, Takasaki, both of Japan

[73] Assignee: Shin-Etsu Chemical Co., Ltd., Tokyo, Japan

[21] Appl. No.: 129,939

[22] Filed: Dec. 3, 1987

[30] Foreign Application Priority Data

Dec. 3, 1986 [JP] Japan .................. 61-288235

[51] Int. Cl.$^4$ .......................................... C07D 251/34
[52] U.S. Cl. ..................................... 544/193; 544/221
[58] Field of Search ............................ 544/221, 193

[56] References Cited

U.S. PATENT DOCUMENTS

| | | | |
|---|---|---|---|
| 2,866,801 | 12/1958 | Himel et al. | 544/193 |
| 2,977,360 | 3/1961 | Dixon | 544/193 |
| 3,278,492 | 10/1966 | Herbstman | 544/193 |
| 3,598,852 | 8/1971 | Berger | 260/443.2 |
| 3,920,644 | 11/1975 | Handa et al. | 544/193 |
| 4,382,125 | 5/1983 | Narayan et al. | 544/193 |
| 4,540,781 | 9/1985 | Barsa | 544/193 |
| 4,654,428 | 3/1987 | Kurashima et al. | 556/414 |

FOREIGN PATENT DOCUMENTS 1579902 9/1968 France .
61-145188 7/1986 Japan .

*Primary Examiner*—John M. Ford
*Attorney, Agent, or Firm*—Lowe, Price, LeBlanc, Becker & Shur

[57] ABSTRACT

A method for preparing a cyclic isocyanuric ester having organosilicon groups which comprises thermally treating an isocyanic ester for addition reaction in the presence of an alkali metal hydroxide or alkoxide. By the above reaction, a cyclic trimer of the starting isocyanic ester can be selectively obtained. The catalyst can be readily removed from the reaction system.

15 Claims, No Drawings

METHOD FOR PREPARING A CYCLIC ISOCYANURIC ESTER HAVING ORGANOSILICON GROUPS

BACKGROUND OF THE INVENTION

1. Field of The Invention

This invention relates to the art of additives for organosiloxane composition and more particularly, to a method for preparing an organosilicon group-bearing cyclic isocyanuric ester in high efficiency. The ester is very useful as an accelerator or promotor for adhesion of room temperature vulcanizable organosiloxane compositions or an additive for organosiloxane compositions suitable for fiber treatment.

2. Description of the Prior Art

For the production of an organosilicon group-containing isocyanuric ester, there is known a process in which hydrogen silane is added to the allyl group of allyl isocyanurate in the presence of a catalyst such as platinum, rhodium or the like. This process is described in French Patent No. 1,579,902. However, this process requires a large amount of the catalyst because the isocyanuric acid ring serves as an inhibitor for the addition reaction. In addition, a one molecule-addition product and a two molecule-addition product are secondarily formed, thus making it difficult to obtain a three molecule-addition product or trimer alone.

U.S. Pat. No. 3,598,852 describes a process of the cyclic isocyanuric ester in which chloropropyl silane ($\equiv$Si(CH$_2$)$_3$Cl) and potassium cyanate (KOCN) are reacted in a polar solvent such as dimethylformamide. This process essentially requires the use of the polar solvent, which, in turn, requires removal of the solvent so as to purify an intended product. However, complete removal of the polar solvent even by vacuum stripping will be difficult.

SUMMARY OF THE INVENTION

It is an object of the invention to provide a method for preparing an organosilicon group-bearing cyclic isocyanuric ester in which the ester can be prepared simply and in a high efficiency by thermal treatment of a starting isocyanic ester.

It is another object of the invention to provide a method for preparing the ester mentioned above in which a catalyst and/or a solvent used for the preparation can be readily removed without difficulty.

The above objects can be achieved, according to the invention, by a method which comprises:

thermally treating or heating an isocyanic ester of the following general formula (1) at a temperature sufficient for cyclization reaction of the isocyanic ester $$(R^1O)_{3-n}(CH_3)_nSi(CH_2)_3NCO \tag{1}$$

in which $R^1$ represents a monovalent hydrocarbon group having from 1 to 4 carbon atoms, and n is 0 or 1, in the presence of a basic catalyst of the formula, $MOR^2$, in which $R^2$ represents a hydrogen atom or a monovalent hydrocarbon group having from 1 to 5 carbon atoms and M represents an alkali meal to obtain a organosilicon group-bearing cyclic isocyanuric ester of the following general formula (2)

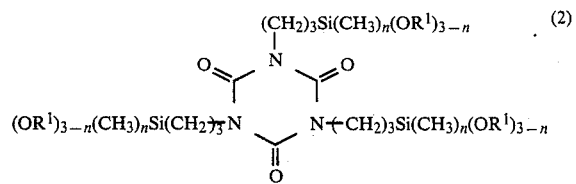

in which $R^1$ and n have, respectively, the same meanings as defined above. If necessary, the catalyst may be removed from the reaction system in a manner as will be described hereinafter.

DETAILED DESCRIPTION OF THE INVENTION

As defined above, the organosilicon group-bearing cyclic isocyanuric ester of the formula (2) is obtained by thermally treating a starting isocyanic ester of the formula (1) in the presence of a basic catalyst. The cyclic isocyanuric ester (2) is a three moleucle-addition product or trimer of the starting isocyanic ester (1). According to the method of the invention, the trimer alone of the isocyanic ester (1) can be selectively obtained in high yield.

The starting isocyanic ester used in the present invention is a compound of the following general formula $$(R^1O)_{3-n}(CH_3)_nSi(CH_2)_3NCO$$

in which $R^1$ is a monovalent hydrocarbon group having from 1 to 4 carbon atoms, and n is 0 or 1. In order to enable the final product to have a high rate of hydrolysis, the monovalent hydrocarbon groups represented by $R^1$ in the above formula are preferably alkyl groups such as a methyl group, an ethyl group, a propyl group and a butyl group, of which a methyl or ethyl group is preferred.

Specific examples of the isocyanic ester include 3-(dimethoxymethylsilyl)propyl isocyanate, 3-(trimethoxysilyl)propyl isocyanate, 3-(tripropoxysilyl)propyl isocyanate, 3-(dibutoxymethylsilyl)propyl isocyanate, and 3-(tributoxysilyl)propyl isocyanate.

The isocyanic ester is readily obtained by a procedure which comprises reacting 3-aminopropylsilane and phosgene in the presence of a tertiary amine as described, for example, in Japanese Laid-open Patent Application No. 61-145188.

In practice, the starting isocyanic ester is subjected to cyclization reaction under heating conditions in the presence of a basic catalyst of the formula, $MOR^2$, in which $R^2$ is a hydrogen atom or a monovalent hydrocarbon group, and M is an alkali meal such as lithium, sodium, potassium, cesium and the like. The basic catalyst useful in the present invention are alkali metal hydroxides or alkoxide.s Examples of the alkoxides include methoxides, ethoxides, propoxides may be used singly or in combination. Other organic alkali metal compounds are not favorable in the practice of the invention. For instance, alkali metal carboxylates such as potassium acetate or potassium propionate are basic in nature but exhibit only a low catalytic activity. when compounds of the above general formula in which $R^2$ represents an aromatic group, e.g. an alkali metal phenoxide, are used, the basicity is weak and is highly soluble in the final isocyanuric ester and a solvent. This leads to the disadvantage that removal of the alkali metal phenoxide form the reaction system is difficult after completion of the reaction. These disadvantages can be overcome when using the alkali metal hydroxides or alkoxides as the catalyst in the practice of the invention.

The amount of the basic catalyst is generally not less than 0.1 parts by weight per 100 parts by weight of a starting isocyanic ester. In view of the reaction time and the ease in separation, the amount is preferably in the range of from 0.1 to 5.0 parts by weight per 100 parts by weight of the isocyanic ester.

The alkali metal hydroxides or alkoxides used as the catalyst generally are not dissolved completely in the reaction system although they may be partially dissolved in the system. These compounds are not necessarily removed from a final product, depending upon the purpose in end use. If it is necessary to remove the catalyst from the reaction system, a diluent such as a non-polar hydrocarbon compound may be added to the system so as to cause a partially dissolved catalyst to completely precipitate and also to facilitate the removal of the reaction system which may be viscous. Subsequently, the catalyst including the precipitated catalyst can be removed form the system such as by filtration. Such non-polar hydrocarbon compounds may be those indicated hereinafter with respect to a solvent for the cyclization reaction. Alternatively, the reaction system containing the catalyst may be treated with insoluble acidic solid materials such a acid clay, silica gel, alumina and the like and subjected to filtration, by which the basic catalyst can be completely removed.

The cyclization reaction of the isocyanic ester of the formula (1) into the organosilicon group-containing cyclic isocyanuric ester of the formula (2) proceeds by thermal treatment or heating of the ester of the formula (1) in the presence of the above basic catalyst. The thermal treatment temperature may, more or less, depend on the type of catalyst, and the presence or absence and the type of solvent. Preferably, the temperature is in the range of from 80° to 150° C., more preferably from 100° to 130° C.

The process of the invention may be conducted in the absence or presence of a solvent. If a solvent is used, a non-polar, inert hydrocarbon compound having a boiling point of from 80° to 150° C. is suitable for this purpose. In short, the reaction using a solvent can be effected under reflux of a solvent used. Specific examples of the non-polar hydrocarbon solvents include benzene, toluene, xylene, hexane, heptane and the like, used singly or in combination. These solvents can be readily removed such as by distillation, if necessary, under reduced pressure, after completion of the cyclization reaction. Moreover, when the solvent is used, the catalyst is allowed to precipitate if partially dissolved and can thus be readily removed as a whole. If any solvent is not used, a non-polar hydrocarbon compound as indicated above should preferably be added to the reaction system after completion of the reaction in order to permit a partially dissolved catalyst to precipitate. Then, the catalyst including the precipitated catalyst is removed such as by filtration.

The present invention is more particularly described by way of examples.

EXAMPLE 1

0.5 g of potassium t-butoxide was charged into a reactor flask and heated to 120° C. Under sufficient agitation, 47.0 g (0.25 moles) of 3-(dimethoxymethylsilyl)propyl isocyanate was dropped into the flask in 20 to 25 minutes, followed by reaction for further 5 to 10 minutes and cooling down to room temperature. Thereafter, the reaction system was diluted with 100 ml of n-hexane to precipitate the catalyst as a whole. The catalyst was subsequently removed by filtraton and the resultant filtrate was concentrated under reduced pressure to obtain 42.3 g (yield 90%) of crystals having a melting point of 46° C.

The crystals were subjected to infrared and gas mass spectrometric analysis, revealing that a peak (2275 cm$^{-1}$) derived from the isocyanate group disappeared and a peak (1690 cm$^{-1}$)corresponding to the isocyanurate group was observed, which was in coincidence with a peak of a reference compound. Because a molecular ion peak was recognized at 567 in the gas mass spectrum, the crystal product was confirmed to be 1,3,5-tris[3-(dimethoxymethylsilyl)propyl]isocyanurate.

EXAMPLE 2

The general procedure of Example 1 was repeated except that there were used, instead of 3-(dimethoxymethylsilyl)propyl isocyanate, 3-(trimethoxysilyl)propyl isocyanate, 3-(diethoxymethylsilyl)propyl isocyanate, and 3-(triethoxysilyl)propyl isocyanate, and 1 wt % of potassium t-butoxide was used and heated to 120° to 130° C. The resultant products were compared for identification with the respective reference compounds with respect to the infrared absorption spectrum and the molecular ion peak in gas mass spectrum. As a result, it was found that corresponding isocyanuric esters were, respectively, obtained from the starting isocyanates. The products and yields are shown in Table 1 below.

TABLE 1

| Starting Isocyanic Ester | $(R^1O)_{n-3}$ | Product | Yield |
|---|---|---|---|
| 3-(trimethoxysilyl)-propyl isocyanate | $(CH_3O)_3$ | 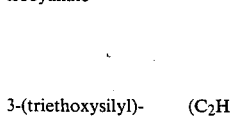 | 90 |
| 3-(diethoxymethylsilyl)propyl isocyanate | $(C_2H_5O)_2$ | | 95 |
| 3-(triethoxysilyl)-propyl isocyanate | $(C_2H_5O)_3$ | R: $(CH_2)_3Si—(OR^1)_{3-n}$ $(CH_3)_n$ | 95 |

EXAMPLE 3

0.6 g of potassium t-butoxide and 100 ml of toluene were charged into a reaction flask and heated to a reflux temperature of the toluene, followed by dropping 62 g (0.25 moles) of 3-(triethyoxysilyl)propyl isocyanate n 20 to 25 minutes under agitation and reaction under reflux for 5 to 10 minutes. After cooling down to room temperature, 50 ml of tuluene was further added so as to cause a dissolved catalyst to precipitate. The caalyst was separated by filtration and the resultant filtrate was concentrated to obtain 59.5 g (yield 96%) of a product. The thus obtained product was subjected to infrared absorption spectroscopy for comparison with a reference compound and also to measurement of molecular weight by gas mass spectroscopy. As a result, it was confirmed that the product was 1,3,5-tris[3-(triethoxysilyl)propyl] isocyanurate.

EXAMPLE 4

The general procedure of Example 1 was repeated except that potassium t-butoxide was replaced by 0.5 g of cesium hydroxide, thereby obtaining 43.7 g (yield 93%) of 1k3,5-tris-[3-(dimethoxymethylsilyl)propyl] isocyanurate.

EXAMPLE 5

Starting 3-(dimethoxymethylsilyl)propyl isocyanate was reacted under different conditions with respect to the type and amount of basic catalyst, the presence or absence of a solvent, the type of solvent if a solvent is used, the reaction temperature and the reaction time indicated in Table 1 below. The results are also shown in Table 1.

TABLE 2

| Experiment No.: | Basic Catalyst | Amount (wt %) | Solvent | Reaction Temp. (°C.) | Reaction Time (Hrs) | Yield (%) |
|---|---|---|---|---|---|---|
| 1 | potassium t-butoxide | 2.0 | — | 120–130 | 0.5 | 90 |
| 2 | " | 0.5 | — | " | 6.0 | 85 |
| 3 | " | 0.1 | — | " | 6.0 | 70* |
| 4 | " | 1.0 | toluene | 110–120 | 0.5 | 96 |
| 5 | " | " | xylene | 120–130 | 0.5 | 95 |
| 6 | potassium methoxide | " | — | " | 0.5 | 91 |
| 7 | sodium methoxide | " | — | 120–130 | 12.0 | 78** |
| 8 | " | " | toluene | 110–120 | 2.0 | 85* |
| 9 | potassium hydroxide | " | — | 120–130 | 6.5 | 80* |
| 10 | lithium hydroxide | " | — | " | 3.0 | 50* |
| 11 | " | " | toluene | 110–120 | 3.0 | 70* |
| 12 | lithium t-butoxide | " | — | 120–130 | 0.5 | 90 |

Note:
*Corresponding isocyanic esters were left partially unreacted, and the respective yields were calculated from an infrared absorption spectrum.
**A corresponding isocyanic ester completely dissapeared but a liquid by-product started to be formed with a lowering of the yield.

Note: *Corresponding isocyanic esters were left partially unreacted, and the respective yields were calculated from an infrared absorption spectrum.

** A corresponding isocyanic ester completely disappeared but a liquid by-product started to be formed with a lowering of the yield.

What is claimed is:

1. A method for preparing an organosilicon group-containing cyclic isocyanuric ester, the method comprising:
thermally treating or heating an isocyanic ester of the following formula (1) at a temperature sufficient for cyclization reaction of the isocyanic ester $$(R^1O)_{3-n}(CH_3)_nSi(CH_2)_3NCO \qquad (1)$$

in which $R^1$ represents an alkyl group having from 1 to 4 carbon atoms, and n is 0 or 1, for cyclization reaction in the presence of a basic catalyst of the formula, $MOR^2$, in which $R^2$ represents a hydrogen atom or an alkyl group having from 1 to 5 carbon atoms and M represents an alkali metal to obtain an organosilicon group-bearing cyclic isocyanuric ester of the following formula (2)

$$(OR^1)_{3-n}(CH_3)_nSi(CH_2)_3N\underset{\underset{O}{\parallel}}{\overset{\overset{(CH_2)_3Si(CH_3)_n(OR^1)_{3-n}}{|}}{\underset{N}{\overset{O}{\diagdown}}\diagup\underset{\diagdown}{\overset{O}{\diagup}}}}N{\text{-}}(CH_2)_3Si(CH_3)_n(OR^1)_{3-n} \qquad (2)$$

in which $R^1$ and n have, respectively, the same meanings as defined above.

2. A method according to claim 1, wherein $R^1$ in the formulae (1) and (2) is a methyl or ethyl group.

3. A method according to claim 1, wherein said basic catalyst is an alkali metal hyroxide.

4. A method according to claim 1, wherein said basic catalyst is an alkali metal alkoxide.

5. A method according to claim 1, wherein said alkali metal is lithium, sodium, potassium or cesium.

6. A method according to claim 1, wherein the thermal treatment is effected in the absence of a solvent.

7. A method according to claim 6, wherein the reaction mixture prior to the removal of the catalyst is cooled down to normal temperatures, to which a non-polar solvent is added thereby causing a partially dissolved catalyst to precipitate and the catalyst including the precipitated catalyst is removed from the reaction mixture.

8. A method according to claim 7, further comprising concentrating the reaction product from which the catalyst has been removed, to obtain the isocyanuric ester.

9. A method according to claim 1, wherein the thermal treatment is effected in the presence of a non-polar, inert hydrocarbon solvent.

10. A method according to claim 9, wherein a reaction mixture prior to the removal of the catalyst, is cooled down to normal temperatures, a non-polar solvent is further added to the reaction mixture to cause a partialy dissolved catalyst to precipitate, and the catalyst including the precipitated catalyst is removed from the reaction mixture.

11. A method according to claim 10, wherein the reaction mixture from which the catalyst has been removed is concentrated to remove the non-polar solvent to obtain the isocyanuric ester.

12. A method according to claim 1, wherein the basic catalyst is used in an amount of not less than 0.1 part by weight per 100 aprts by weight of the isocyanic ester.

13. A method according to claim 1, wherein the thermal treatment is effected at a temperature of from 80° to 150° C.

14. A method according to claim 1, wherein said thermal treatment step is conducted in the absence of a polar solvent.

15. A method according to claim 1, wherein said thermal treatment step is conducted in the absence of dimethylformamide.

* * * * *